United States Patent
Wang

(10) Patent No.: US 9,228,936 B2
(45) Date of Patent: Jan. 5, 2016

(54) BIREFRINGENCE MEASUREMENT OF POLYCRYSTALLINE SILICON SAMPLES OR THE LIKE

(71) Applicant: Hinds Instruments, Inc., Hillsboro, OR (US)

(72) Inventor: Baoliang Wang, Beaverton, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 65 days.

(21) Appl. No.: 14/095,833

(22) Filed: Dec. 3, 2013

(65) Prior Publication Data

US 2015/0153270 A1    Jun. 4, 2015

(51) Int. Cl.
*G01N 21/23* (2006.01)

(52) U.S. Cl.
CPC .................................. *G01N 21/23* (2013.01)

(58) Field of Classification Search
None
See application file for complete search history.

(56) References Cited

U.S. PATENT DOCUMENTS

| | | |
|---|---|---|
| 2,773,413 A | 12/1956 | Schade, Sr. |
| 3,447,874 A | 6/1969 | Back |
| 3,502,413 A | 3/1970 | Lightner |
| 3,544,796 A | 12/1970 | Baker |
| 3,714,372 A | 1/1973 | Rosen |
| 3,990,798 A | 11/1976 | White |
| 4,050,085 A | 9/1977 | Prince |
| 4,307,294 A | 12/1981 | Campbell |
| 5,028,125 A | 7/1991 | Kikuchi |
| 5,239,171 A | 8/1993 | Takabayashi |
| 5,656,356 A | 8/1997 | Masuda et al. |
| 5,864,403 A * | 1/1999 | Ajji et al. ..................... 356/365 |
| 6,091,075 A | 7/2000 | Shibata |
| 6,266,141 B1 | 7/2001 | Morita |
| 6,583,877 B2 | 6/2003 | Norton |
| 6,985,227 B2 | 1/2006 | Wang |
| 6,985,288 B2 | 1/2006 | Miyashita |
| 7,609,958 B2 | 10/2009 | Border |
| 8,248,605 B2 | 8/2012 | Wang |
| 8,520,207 B2 | 8/2013 | Wang |
| 2005/0162743 A1 | 7/2005 | Yano et al. |
| 2005/0184239 A1 | 8/2005 | Abuzaina et al. |
| 2009/0223439 A1* | 9/2009 | Shultz et al. .................... 117/11 |
| 2009/0279089 A1* | 11/2009 | Wang ........................... 356/365 |
| 2009/0323064 A1 | 12/2009 | Wang |
| 2012/0314202 A1 | 12/2012 | Danyluk |
| 2012/0326005 A1 | 12/2012 | Wang |

FOREIGN PATENT DOCUMENTS

JP        11095126 A    4/1999

OTHER PUBLICATIONS

International Search Report and Written Opinion in corresponding PCT application PCT/US/201466989; Jan. 29, 2015; 6 pages.

* cited by examiner

*Primary Examiner* — Gordon J Stock, Jr.
(74) *Attorney, Agent, or Firm* — Klarquist Sparkman, LLP

(57) ABSTRACT

A birefringence measurement system includes a lens mounted for selective movement into and out of use in the optical setup so that a wide range of sample types can be handled by the system without reconfiguring the primary components of the optical setup of the system (moving the detector, changing the light source power, etc.) in a manner that would sacrifice the cost effectiveness, efficiency, mechanical reliability and repeatability of measurements for such systems.

10 Claims, 5 Drawing Sheets

BIREFRINGENCE MEASUREMENT OF POLYCRYSTALLINE SILICON SAMPLES OR THE LIKE

BACKGROUND INFORMATION

This invention relates to birefringence measurement systems, examples of which are described in U.S. Pat. No. 6,985,227, hereby incorporated by reference.

A schematic diagram of an optical setup 20 of one embodiment of such a system is shown in FIG. 1. That system employs as a light source 22 a polarized, 1550-nm diode laser. The light beam B1 from the source 22 passes through a polarizer 24 that is oriented at 45 degrees. The system also includes a photoelastic modulator (PEM) 26 oriented at 0 degrees and operated at 42 KHz. The source 22, polarizer 24, and PEM 26 components of the optical setup are typically secured in a casing or cabinet and are collectively referred to as a source module 28.

A sample holder 30, which can be mounted on a computer-controlled X-Y stage, is located in the path of the optic axis 25 of the optical setup 20, thereby to allow the beam to scan various locations of an optical element or sample 32. The light passing through the sample is then detected for determination of the birefringence of the sample.

The light beam B2 that emanates from the sample (hereafter referred to as the "sampled beam" B2) is directed through another PEM 34 that is oriented at 45 degrees and operated at 47 KHz. After passing through an analyzer 36 oriented at 0 degrees, the sampled beam B2 is directed into the receiving or active area 38 of a Ge-photodiode detector 40. The PEM 34, analyzer 26 and detector 40 components of the optical setup are collectively referred to as a detector module 42 that includes an entrance aperture 44 through which the sampled beam B2 enters the detector module.

The light source beam B1 (in this case, laser light) is well collimated, and compact detectors (that is, having relatively small active areas 38 on the order of 1-6 mm) may be employed, especially where the sample 32 has smooth, parallel surfaces normal to the incident light beam B1, or exhibits other physical characteristics such that the beam path is substantially unaltered in passing through the sample.

The cost effectiveness and efficiency of a birefringence measurement system as just described is enhanced when the system can analyze a wide variety of sample types and sizes. Moreover, it is important to maintain the mechanical reliability and repeatability of measurements for a given system by minimizing or eliminating the need for repositioning the components of the source module 28 and detector module 42 irrespective of changes in the size or shape of the sample.

Some samples for which birefringence measure is desired are shaped or configured so that the sampled beam is spread as a result of diffusion, defocusing, scattering, fanning or other mechanisms. For instance, as diagrammed in FIG. 2, a sample 232 may be formed of material, such as polycrystalline silicon, which will alter the source light beam B1 so that the sampled beam B2 emanating from the sample 232 is spread, as compared to the incident beam B1, such that only a small portion of the light that passes through the sample and then through the entrance aperture 44 will impinge upon the active area 38 of the detector 40. Thus, the intensity of the light reaching the detector 40 is too low for accurate detection that would permit determination of birefringence characteristics of the sample. This effect becomes more problematic when even larger samples are tested. The foregoing problem with beam spreading associated with samples such as polycrystalline silicon or the like will also arise with other types of sample material. For example, single crystal silicon or other material may have a surface roughness that can similarly diffuse or spread the light beam directed through it.

This invention is directed to a method of addressing the foregoing problem attributable to such beam-spreading samples without reconfiguring the optical setup of the birefringence measurement system (by moving the detector, changing the light source power, etc.) in a manner that would sacrifice the cost effectiveness, efficiency, mechanical reliability and repeatability of measurements for such systems. The system of the present invention is thus reliably usable with a wide range of samples, regardless of the size, shape, finish, or other physical characteristics of the material.

DETAILED DESCRIPTION

Figure 1:
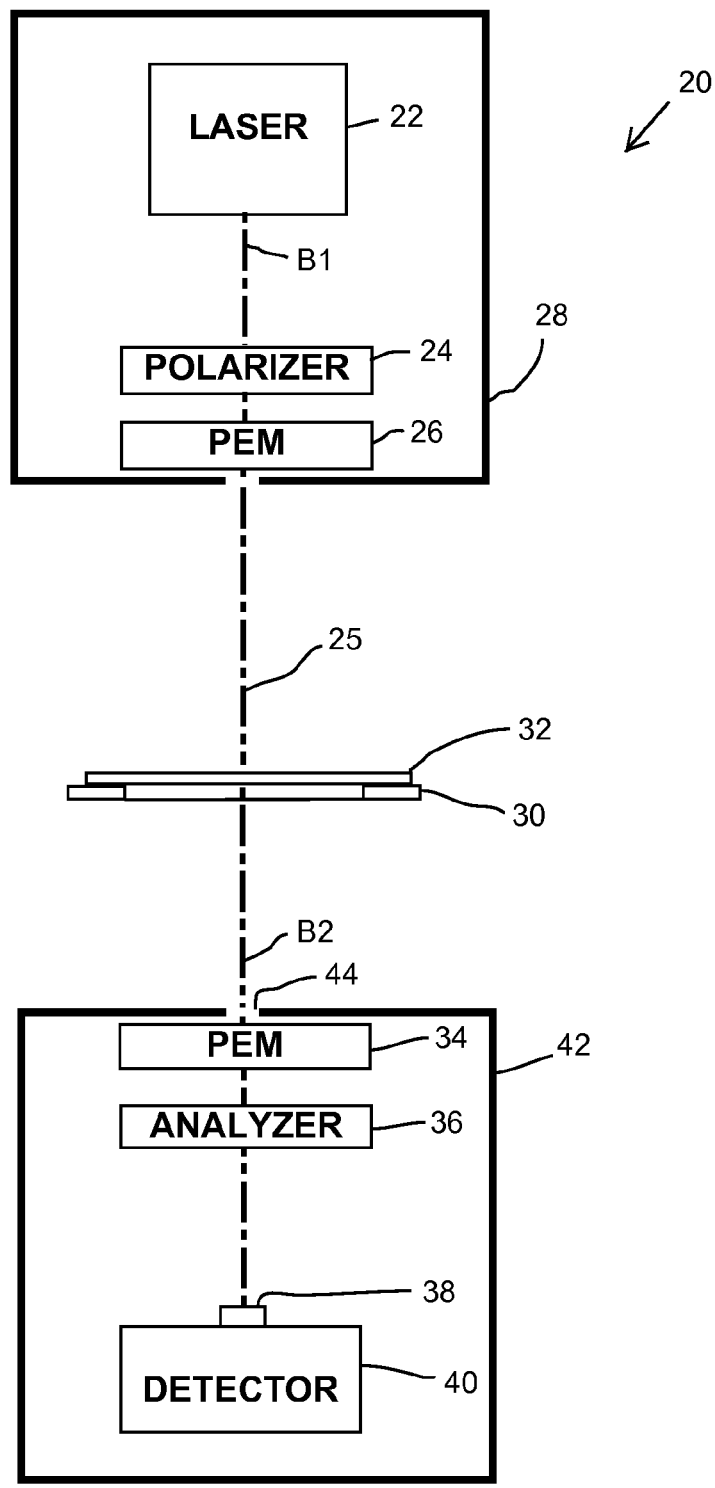
FIG. 1 is a diagram of a birefringence measurement system that is adaptable for carrying out the approach of the present invention.
Figure 3:
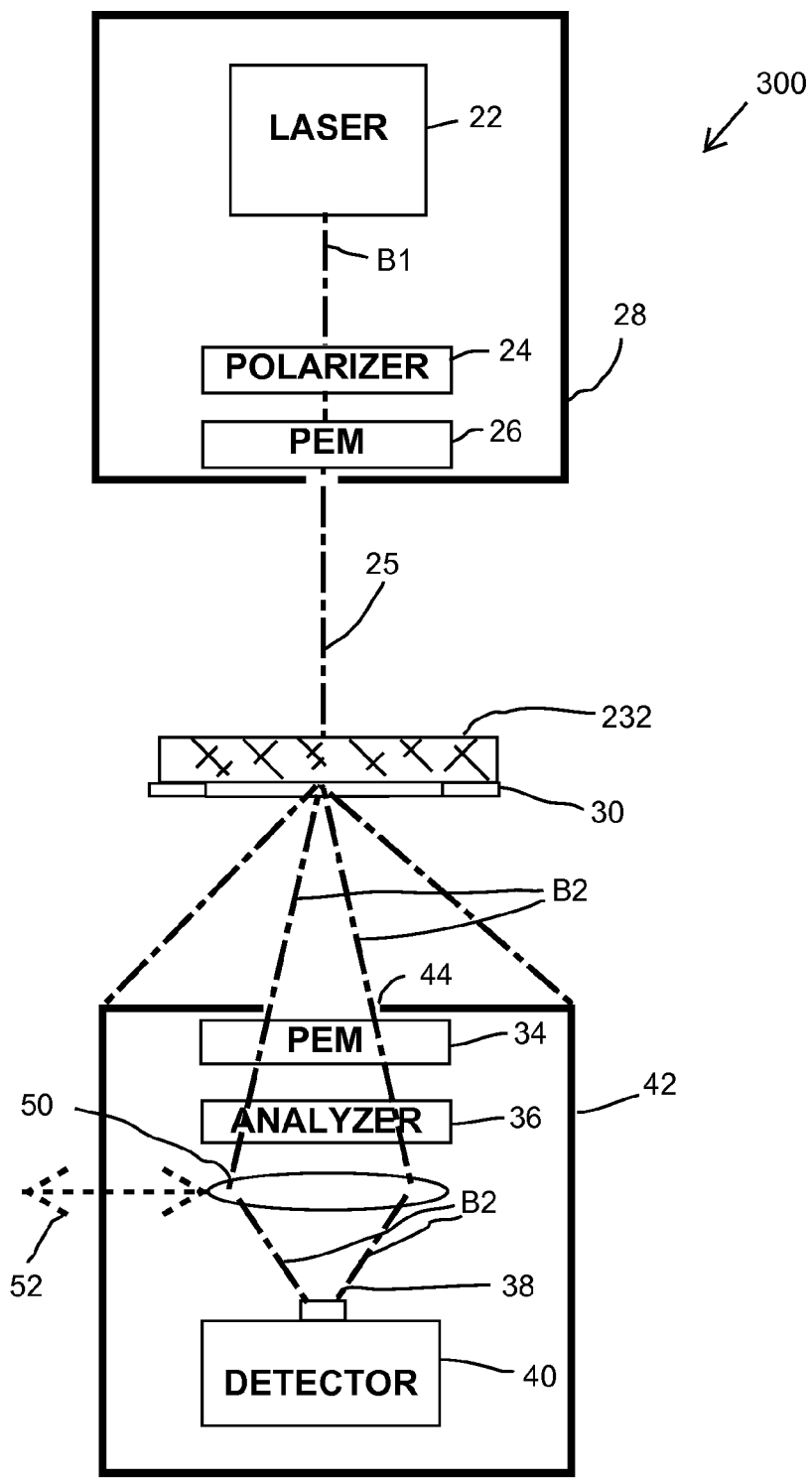
FIG. 3 is a diagram of one preferred embodiment of the invention for solving the beam-spreading/detection problem.

With reference to FIG. 3, many of the components of the optical setup 300 of the birefringence measurement system diagrammed there match those shown in FIG. 1, including the light source 22; polarized, 1550-nm diode laser; source light beam B1; polarizer 24 oriented at 45 degrees; a first photoelastic modulator (PEM) 26 oriented at 0 degrees and operated at 42 KHz; source module 28; sample holder 30; second PEM 34 that is oriented at 45 degrees and operated at 47 KHz; analyzer 36 oriented at 0 degrees; detector 40 with active area 38; and detector module 42 that includes an entrance aperture 44 toward which the sampled, spread beam B2 is directed.

Figure 2:
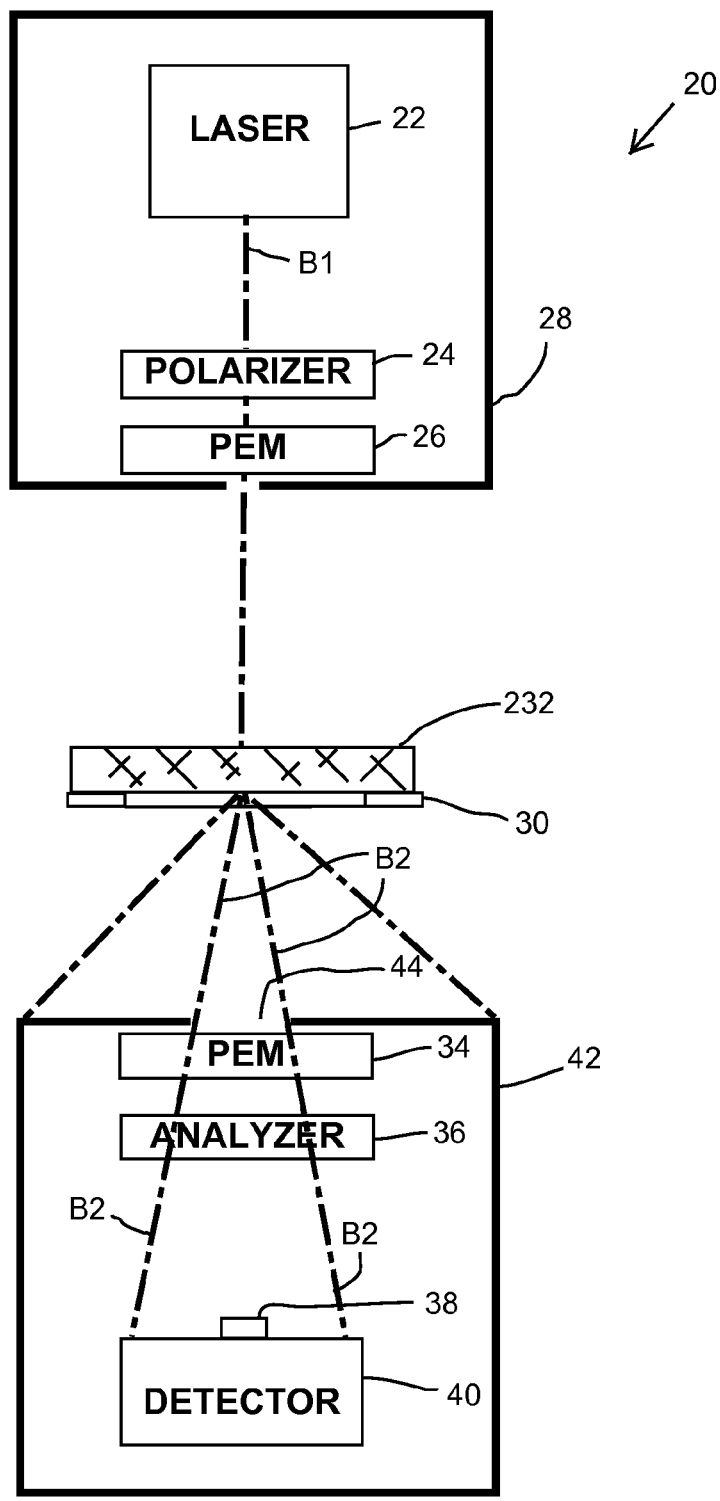
FIG. 2 is a diagram for illustrating a beam-spreading problem when certain types of samples are attempted to be measured in the birefringence measurement system of FIG. 1 prior to adaptation of the present invention.

The sample 232 on the sample holder is, as discussed above in connection with FIG. 2, one that spreads the sampled beam B2 owing to the sample's material makeup or surface roughness, such as a portion of a boule of polycrystalline silicon.

In this embodiment (FIG. 3) a supplemental component is introduced into the optical setup 300 of the system in the form of a focusing lens 50. The lens 50 is preferably located in the detector module 42 between the analyzer 36 and the detector 40. The lens intercepts the spreading or diverging beam B2 that enters the detector module 42 and focuses it so that the energy or intensity of the re-focused beam B2 converges on the active area 38 of the detector to provide a sufficiently high intensity level for detection, which would not have been provided in the absence of the lens 50.

Preferably, the lens 50 is mounted for selective movement into or out of the path of the sampled beam B2, as indicated by the arrow 52. Such movement can be accomplished by any suitable translating or rotating holder for the lens 50. It will be appreciated that the selective positioning of the lens will enable the same detector to be used with samples that do not substantially spread the beam path (FIG. 1) by moving the lens 50 to a position that is retracted from the beam path, and with samples that do spread the beam path (FIGS. 2 and 3, for example) by extending the lens into the path of the beam, as seen in FIG. 3.

It will be appreciated that the position of the lens 50 relative to the sample and detector 40 as well as its power and size is selected so that the converging beam conforms to the numerical aperture of the detector active area 38.

Figure 4:
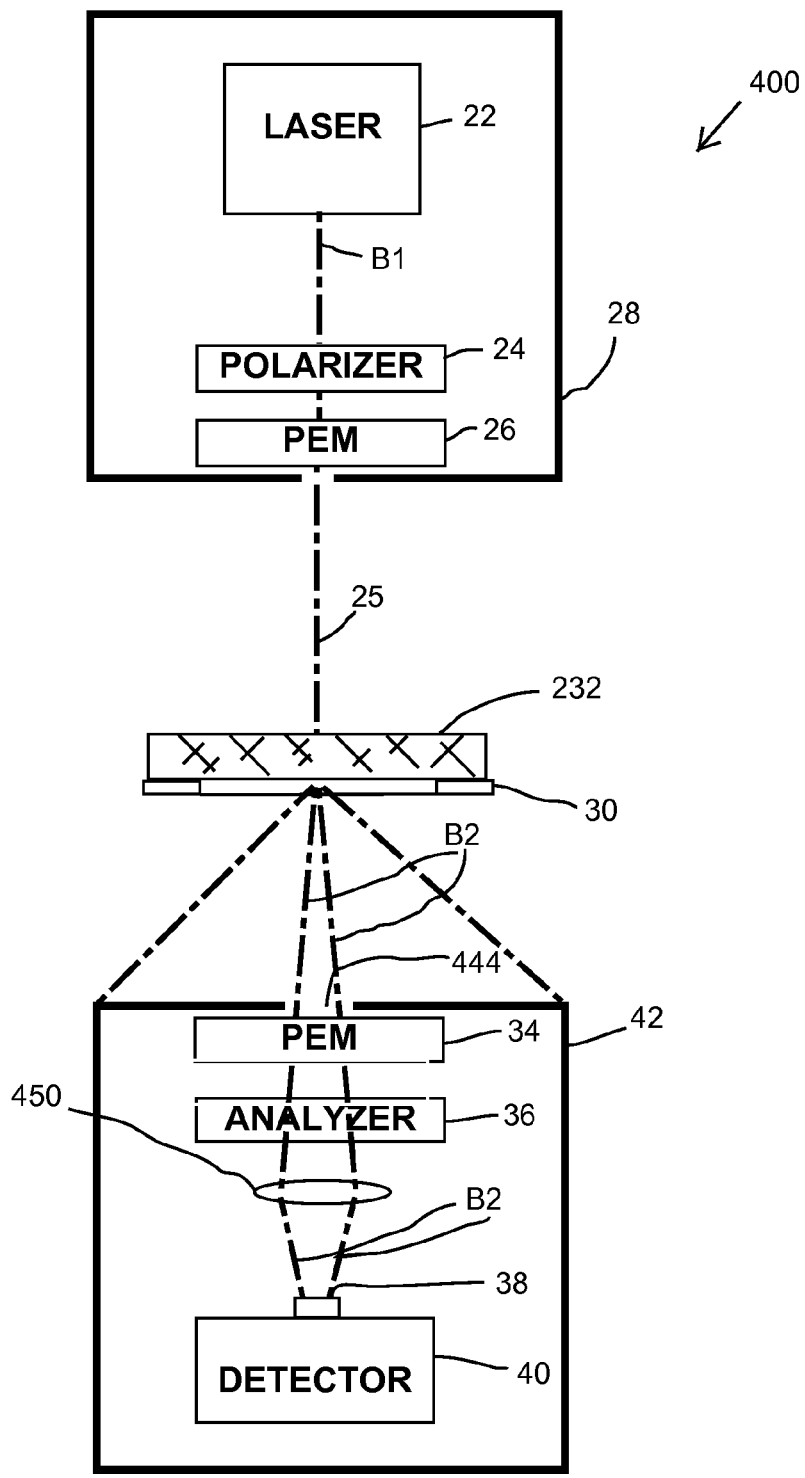
FIG. 4 is a diagram of another preferred embodiment of the invention for solving the beam-spreading/detection problem.

In some instances, the introduction of a relatively high-power focusing lens 50 may introduce into the sampled beam B2 undesirable polarization artifacts. The diagram of FIG. 4 illustrates another preferred embodiment of the invention that substantially reduces or eliminates such polarization artifacts. In this regard, the setup 400 of the embodiment of FIG. 4 corresponds to what is illustrated in FIG. 3, except that the numerical aperture of the entrance aperture 444, which is adjustable, is reduced. This, in turn, enables the use of a smaller focusing lens 450 and attendant reduction or prevention of the lens-induced polarization artifacts.

Figure 5:
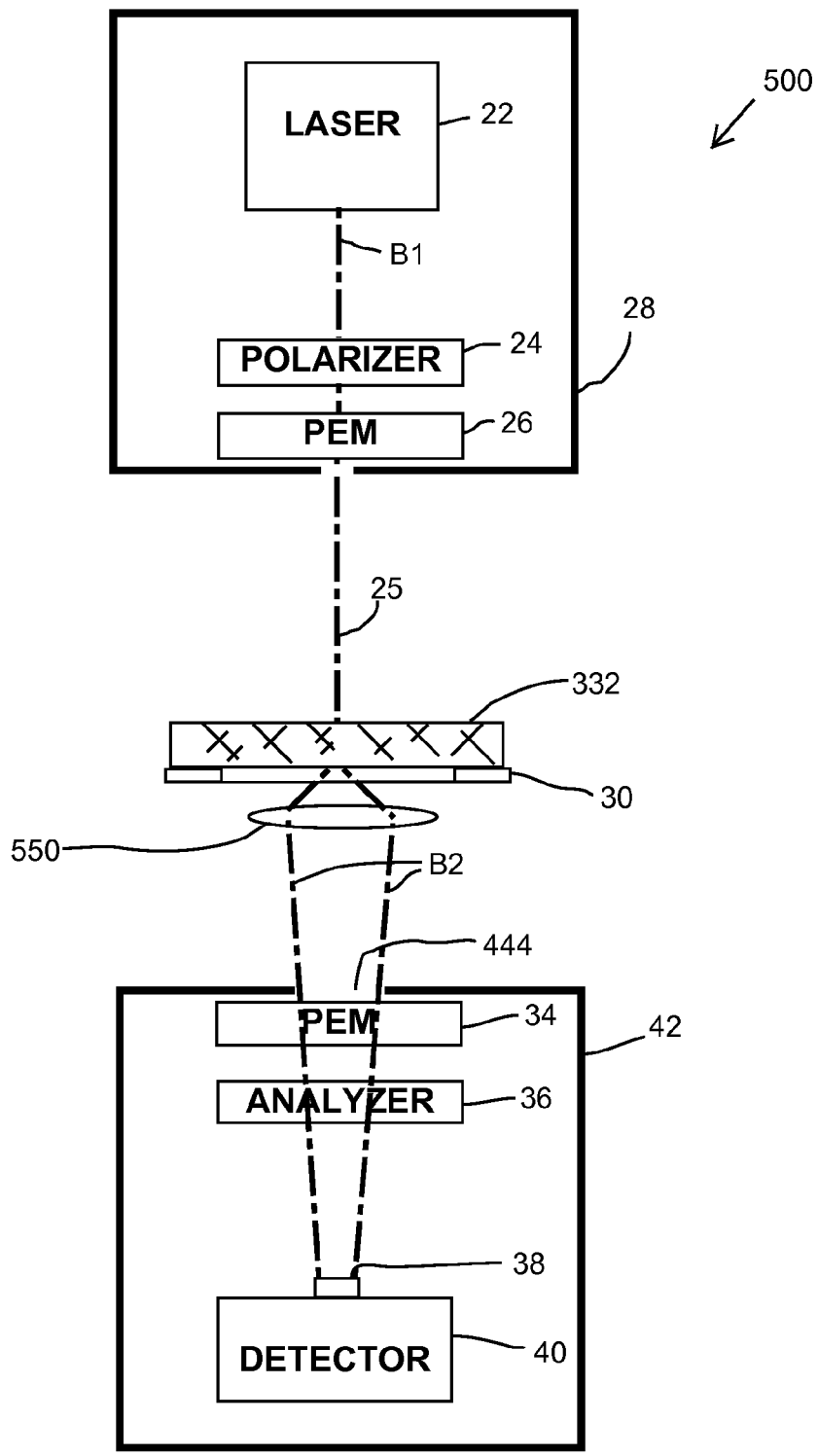
FIG. 5 is a diagram of yet another preferred embodiment of the invention for solving the beam-spreading/detection problem.

In the foregoing embodiments, the outermost portion of the beam B2 that is spread by the sample 232 (that is, the portion farthest from the optical axis 25 of the system along which the source beam B1 is directed), does not pass through the entrance aperture 444 of the detector module 42. In instances when it is desirable to maximize the light intensity reaching the detector 40, the focusing lens 550 (See setup 500 of embodiment of FIG. 5) may be located between the sample 232 and the detector module 42. This greatly increases the light intensity reaching the active area 38 of the detector 40. It will be appreciated that the position of the lens 550, the power of the lens, and the aperture of the lens can be adjusted to control the numerical aperture of the sampled beam B2, and thus the amount of light focused onto the detector. The size of the numerical aperture of the entrance aperture 444 is balanced with the decrease of polarization artifacts, thereby to optimize the system for the particular requirements of the applications and samples under test.

It is noteworthy that the lens 450, 550 can be placed at different positions in the optical axis 25, and that more than one lens (hence, more than one lens location) may be employed. The method described above is not limited to use with laser light sources.

Importantly, since the lens is mounted for selective movement into and out of use in the optical setup (FIG. 3), a wider range of sample types (and the resultant wide range of beam spreading) can be handled by the system without reconfiguring the primary components of the optical setup of the birefringence measurement system (moving the detector, changing the light source power, etc.) in a manner that would sacrifice the cost effectiveness, efficiency, mechanical reliability and repeatability of measurements for such systems.

Put another way, the operational characteristics of the primary components of the optical setup of the birefringence measurement system, such as the detector gain or position in the module; PEM settings or position in the optical setup; or the light source power, need not be changed in instances where the system is adapted to measure both beam-spreading samples as well as samples that do not appreciably spread the sampled beam (beyond the entrance aperture, for example).

The invention claimed is:

1. A method of adapting a birefringence measurement system for measuring beam spreading samples, wherein the system has an optical setup having primary components that include a light source for directing a source beam of light through a sample to propagate from the sample as a sampled beam of light, a detector module that includes an entrance aperture, a photoelastic modulator (PEM), and a detector that has active area for receiving the sampled beam of light for detecting an intensity thereof, the method comprising steps of:

placing a first sample in a path of the source beam of light, the sample being such that it does not spread the sampled beam of light;

detecting light passing through the first sample for use in measuring the birefringence of the first sample;

replacing the first sample with a second sample that spreads the sampled beam of light;

focusing the spread, sampled beam of light to have the focused light impinge upon the active area of the detector; and detecting the light impinging upon the active area for use in measuring the birefringence of the second sample.

2. The method of claim 1 wherein the step of detecting the light impinging upon the active area is carried out without changing operational characteristics of the primary components of the optical setup of the birefringence measurement system.

3. The method of claim 2 wherein the step of focusing the spread, sampled beam of light includes locating at least one focusing lens in the path of the spread, sampled beam of light; and locating the focusing lens out of the path of the sampled beam of light while detecting light passing through the first sample.

4. The method of claim 1 wherein the entrance aperture has a first numerical aperture during the step of detecting light passing through the first sample, and the step of focusing the spread, sampled beam of light includes locating a focusing lens in the path of the spread, sampled beam of light; the method further including a step of reducing the numerical aperture of the entrance aperture while detecting the light impinging upon the active area for use in measuring the birefringence of the second sample.

5. The method of claim 1 including a step of providing as a second sample at least a portion of a boule of polycrystalline silicon.

6. The method of claim 1 including a step of providing as the second sample an optical element having a surface roughness that spreads the beam of light.

7. The method of claim 1 wherein the step focusing the spread, sampled beam of light includes locating at least one focusing lens in the path of the spread, sampled beam of light.

8. The method of claim 7 including a step of locating the focusing lens between the PEM and the active area of the detector.

9. The method of claim 7 including a step of locating the focusing lens between the second sample and the entrance aperture.

10. The method of claim 7 including a step of locating the focusing lens out of the path of the sampled beam of light while detecting light impinging upon the active area for use in measuring the birefringence of the second sample.

* * * * *